United States Patent [19]

Horodysky

[11] Patent Number: 4,529,528

[45] Date of Patent: Jul. 16, 1985

[54] BORATED AMINE-PHOSPHITE REACTION PRODUCT AND LUBRICANT AND FUEL CONTAINING SAME

[75] Inventor: Andrew G. Horodysky, Cherry Hill, N.J.

[73] Assignee: Mobil Oil Corporation, New York, N.Y.

[21] Appl. No.: 561,412

[22] Filed: Dec. 14, 1983

[51] Int. Cl.³ .......................... C10M 1/54; C10M 5/28
[52] U.S. Cl. ............................... 252/49.6; 260/462 R; 260/922
[58] Field of Search .................. 252/49.6; 260/462 R, 260/922

[56] References Cited

U.S. PATENT DOCUMENTS

| | | | |
|---|---|---|---|
| 2,758,971 | 8/1956 | Mikeska | 252/32.7 E |
| 4,273,665 | 6/1981 | Braid | 252/49.6 |
| 4,298,486 | 11/1981 | Horodysky | 252/49.6 |
| 4,370,248 | 1/1983 | Horodysky | 252/49.6 |

Primary Examiner—William R. Dixon, Jr.
Assistant Examiner—C. Johnson
Attorney, Agent, or Firm—Alexander J. McKillop; Michael G. Gilman; Van D. Harrison, Jr.

[57] ABSTRACT

Products of reaction between a bis(2-hydroxyethyl)alkylamine or certain higher oxylated members, a dihydrocarbyl phosphite and a boron compound have been found to be effective friction reducers and fuel reducing additives for internal combustion engines when such products are compounded with lubricants and liquid fuels.

24 Claims, No Drawings

BORATED AMINE-PHOSPHITE REACTION PRODUCT AND LUBRICANT AND FUEL CONTAINING SAME

BACKGROUND OF THE INVENTION

1. Field of the Invention:

This invention relates to novel proeducts of reaction and to their use as lubricant and fuel additives. More particularly, it relates to products of reaction between an alkoxylated amine, dihydrocarbyl phosphites and a boron compound and to their use in the stated media.

2. Discussion of the Prior Art:

The metal surfaces of machinery or engines operating under heavy or normal loads wherein metal is undergoing metal to metal contact even when being lubricated. Thus, there is always metal wear which can be excessive. Often lubricants used to protect the metal surfaces do not completely prevent wear at the points of metal to metal contact. Consequently, the performance of the machine or engine will suffer, and in aggravated cases the machine or engine may become completely inoperative from excessive wear caused the friction.

There have been many attempts to devise additive systems to improve the frictional properties of a lubricant. The phosphate derivatives of the present invention are believed to be capable of overcoming some of the deficiencies of prior art additives and to provide lubricating oil compositions with enhanced friction characteristics.

U.S. Pat. No. 2,758,971 describes a class of metal phosphonates which are disclosed as having properties which prevent breakdown of oils at high temperatures.

U.S. Pat. No. 2,792,374 discloses the alkali metal salts of certain alkyl alkylphosphonic acids as defoamants in aqueous systems.

U.S. Pat. No. 4,356,097 teaches an engine crankcase lubricating oil containing a dihydrocarbyl hydrocarbylphosphonate, which oil exhibits reduced friction.

U.S. Pat. Nos. 3,398,197, 3,711,406, 3,933,659 and 4,129,508 teach that amines and alkoxylated amines are known for their surface activity, lubricity and dispersant properties in lubes and fuels.

The use of certain boron containing compounds is known. For example, see those taught in U.S. Pat. Nos. 4,370,248, 4,298,486 and 4,273,665.

U.S. Pat. No. 2,982,727 discloses lubricating oil compositions containing certain salts of oxygen-containing esters of phosphorus. The esters are phosphonates similar to those described in U.S. Pat. No. 2,758,971.

However, no art is known that teaches or suggests the phosphate ester of the present compositions.

SUMMARY OF THE INVENTION

In accordance with the invention, there are provided products of reaction made by reacting an alkoxylated hydrocarbylamine of the formula

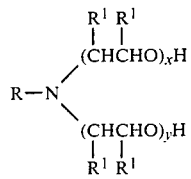

wherein R is a $C_6$ to $C_{30}$ hydrocarbyl group, $R^1$ is hydrogen or a $C_1$ to $C_6$ hydrocarbyl group, preferably a $C_1$ to $C_6$ alkyl group, and x and y are from 0 to about 10, at least one of them being at least 1, preferably from about 1 to about 3, and more preferably both are 1, with (2) a phosphite of the formula

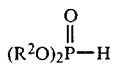

wherein $R^2$ is a $C_1$ to $C_6$ hydrocarbyl group and (3) a boron compound including boric oxide, a metaborate and a compound of the formula

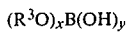

wherein $R^3$ is a $C_1$ to $C_6$ alkyl group and x and y are 0 to 3, their sum being 3.

The invention also provides lubricant and liquid fuel compositions containing the product and a method of reducing the fuel consumption of an internal combustion engine by lubricating, fueling or lubricating and fueling said engine with the appropriate lubricant and fuel compositions.

As used herein "hydrocarbyl" is preferably an alkyl group. It may also be selected from an alkaryl, aralkyl, alkenyl, cycloalkyl or cycloalkenyl group.

BACKGROUND OF THE INVENTION

The compounds of the invention can be made by first reacting the amine and the phosphite followed by reaction of the product thus obtained with the boron compound. Alternatively they can be made by reacting the amine and boron compound first, then reacting the phosphite with this product.

In general, the reaction conditions are not critical. Reaction temperatures for reaction of the amine, either with the phosphite or boron compound as the first reaction, can take place at from about 60° C. to about 260° C., preferably about 80° C. to about 180° C. The second reaction, again whether with the phosphite or boron compound, can occur within the range of from about 60° C. to about 260° C., preferably from about 80° C. to about 180° C.

When carrying out the first-mentioned reaction, i.e., amine plus phosphite followed by boron compound, the amine is reacted with phosphite so that at least about 5% but not more than about 95% of the amine hydroxyl groups are reacted with phosphite. This intermediate product can have as little as 5% of the remaining amine hydroxyl groups reacted with a boron compound, but can have all of such groups borated. When all groups are to be borated, an additional 50% to 100% excess of boron compound can be used to form a product containing extra boron. In the alternative reaction, the amine is first reacted with the boron to the same extent as with the phosphite and this intermediate is then reacted with phosphite so that at least about 5% and up to 95% of the amine hydroxyls are phosphated. When all hydroxy groups ar phosphated, the phosphite can be used in excess, e.g., from about 50% to 100% excess.

Hydrocarbon solvents, or other inert solvents may be used in the reaction. Included among the useful solvents are benzene, toluene and xylene. In general, any hydrocarbon solvent can be used in which the reactants are soluble and which, can, if the products are soluble therein, by easily removed. For the boration reaction, alcoholic solvents such as ethanol, propanol, butanol and hexamethylene glycol can be used.

The useful alkoxylated amines include 2-hydroxyethylhexylamine, 2-hydroxyethyloctylamine, 2-hydroxyethyldodecylamine, 2-hydroxyethyltetradecylamine, 2-hydroxyethylpentadecylamine, 2-hydroxyethyleicosylamine, 2-hydroxyethyltriacontylamine, 2-hydroxyethyloleylamine, 2-hydroxyethyltallowamine, 2-hydroxyethylsoyamine, bis(2-hydroxyethyl)hexylamine, bis(2-hydroxyethyl)octylamine, bis(2-hydroxyethyl)dodecylamine, bis(2-hydroxyethyl)tetradecylaminee, bis(2-hydroxyethyl)pentadecylamine, bis(2-hydroxyethyl)eicosylamine, bis(2-hydroxyethyl)triacontylamine, bis(2-hydroxyethyl)oleylamine, bis(2-hydroxyethyl)tallowamine, bis(2-hydroxyethyl)soyamine, 2-hydroxylpropylhexylamine, 2-hydroxypropyloctylamine, 2-hydroxypropyldodecylamine, 2-hydroxypropyltetradecylamine, 2-hydroxypropylpentadecylamine, 2-hydroxypropyleicosylamine, 2-hydroxypropyltriacontylamine, 2-hydroxypropyloleylamine, 2-hydroxypropyltallowamine, 2-hydroxypropylsoyamine, bis(2-hydroxypropyl)hexylamine, bis(2-hydroxypropyl)octylamine, bis(2-hydroxypropyl)dodecylamine, bis(2-hydroxypropyl)tetradecylamine, bis(2-hydroxypropyl)pentadecylamine, bis(2-hydroxypropyl)eicosylamine, bis(2-hydroxypropyl)triacontylamine, bis(2-hydroxypropyl)oleylamine, bis(2-hydroxypropyl)tallowamine, bis(2-hydroxypropyl)soyamine and mixtures thereof. Also included are the comparable members wherein in the above formula at least one of x and y is at least 2, as for example, 2-hydroxyethoxyethylhexylamine.

The preferred phosphites are dimethyl phosphite, diethyl phosphite, dipropyl phosphite, dibutyl phosphite, diamyl phosphite and dihexyl phosphite.

The boron compounds, in addition to boric oxide and the metaborates, include boric acid, mono-, di- and trimethyl borates, mono-, di and tripropyl borates, mono-, di- and tributyl borates, mono-, di- and triamyl borates and mono-, di- and trihexyl borates, and silica borates.

The structure of the products of this invention are not known and are therefore referred to in the specification and appended claims as products of reaction, reaction products or an equivalent expression. As an illustration, the reaction products from amine and phosphite can range from the simple to the complex. Each illustrated intermediate product will have more than one, and perhaps all of the following proposed compounds, with which the boron compound will react. It will be understood that the structures are shown only to illustrate the types of compounds one can expect to find in the reaction product. It will also be understood that the mix of compounds in a particular reaction product will depend on the proportion of reactants. Thus, when one reacts, for example, one mole of a bis(2-hydroxyethyl)alkylamine, the following compounds are possible.

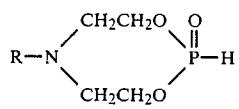

I

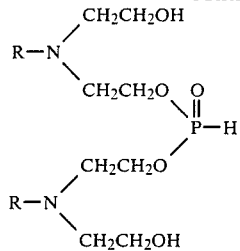

II

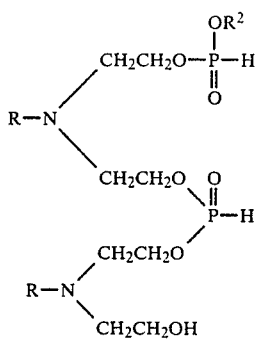

III

The isomer of III

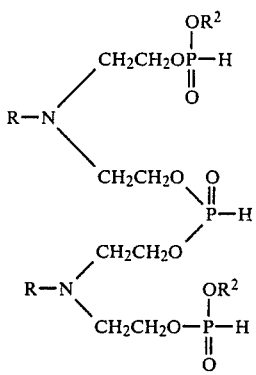

IV

This intermediates mixture can then be reacted with the boronating agent to form the boron-containing amine phosphites disclosed.

It will be understood by one in the chemical arts that many other products are possible. For example, III and IV can be polymerized by further reaction of amine with the free $R^2O$ groups.

The lubricants contemplated for use with the esters herein disclosed include mineral and synthetic hydrocarbon oils of lubricating viscosity, mixtures of mineral oils and synthetic oils and greases from any of these, including the mixtures. The synthetic hydrocarbon oils include long-chain alkanes such as cetanes and olefin polymers such as oligomers of hexene, octene, decene, and dodencene, etc. These borated amine phosphites are especially effective in synthetic oils formulated using mixtures of synthetic hydrocarbon olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids.

Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils. Often preferred are thickeners containing at least a significant amount (of at least 1%) of lithium 12-hydroxystearate soap derived from the hydroxystearate ester, glycerides or acid.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15 percent by weight of the total grease composition.

The liquid fuels contemplated include the liquid hydrocarbons, such as gasoline, fuel oil and diesel oil and the liquid alchols such as methyl alcohol and ethyl alcohol. The fuels also include mixtures of alcohols as well as mixtures of alcohols and liquid hydrocarbons.

The compounds of the invention are used with lubricating oils or greases to the extent of from about 0.1% to about 10% by weight of the total composition, preferably from about 0.2% to about 2% and with fuels to the extent of from about 5 lbs. to about 250 lbs. per 1000 bbls. of fuel. Furthermore, other additives, such as detergents, antioxidants, antiwear agents and the like may be present. These can include metal (e.g., calcium and magnesium) phenates and sulfonates; polymeric succinimides; zinc, nickel or cadmium dialkyl or diaryl dithiophosphates, including zinc dialkyl dithiophosphates wherein the alkyl portion is derived from propanol, butanol, pentanol, hexanol, octanol or octadecanol; polymers; calcium and magnesium salts; and polymeric viscosity index improving additives such as olefin copolymers, sulfurized olefins and the like.

The following Examples will present illustrations of the invention. They are illustrative only, and are not meant to limit the invention.

EXAMPLE 1

Boron-Containing Phosphite of Bis(2-Hydroxyethyl)oleylamine

Part A

Approximately 240 g of bis(2-hydroxyethyl)oleylamine (obtained as Ethomeen 0/12 from Armak Chemical Company) and 34 g of dimethyl hydrogen phosphite were charged to a one liter reactor equipped with heater, agitator, provision for blanketing vapor space with nitrogen and Dean-Stark tube with condenser. The reactor was heated to about 120° C. for 2 hours, 140° C. for 3 hours and 152° C. for 1 hour, during which time evolution of methanol diminished and appeared to cease. The crude product was vacuum stripped at 152° C. for ½ hour to remove volatile materials.

Part B

Approximately 125 g of the intermediate of Part A, 100 g of toluene, and 7 g of boric acid were charged to a 500 ml reactor equipped as generally described in Part A. The reactor contents were heated to 145° C. over a period of about 6 hours until water evolution as a result of azeotropic distillation ceased. Approximately 6 g of water were collected. The solvent was removed by vacuum distillation at 145° C. and the reactor contents were filtered through diatomaceous earth.

EXAMPLE 2

Boron-Containing Phosphite of Bis(2-Hydroxyethyl)soyamine

Part A

Approximately 240 g of bis(2-hydroxyethyl)soyamine (obtained as Ethomeen S/12 from Armak Chemical Co.) and 34 g of dimethyl hydrogen phosphite were charged to a reactor equipped as generally described in Example 1. The reactor contents were heated to 120° C. for 2 hours, 140° C. for 3 hours and 150° C. for 1 hour, during which latter time, evolution of methanol diminished and ceased. The crude product was then vacuum stripped at 150° C. to remove volatile materials.

Part B

Approximately 125 g of the intermediate of Part A, 100 g of toluene and 7 g of boric acid were charged to a 500 ml reactor equipped as generally described in Part A. The reactor contents were heated up to 145° C. until water evolution as a result of azeotropic distillation ceased. Approximately 5 g were collected. The solvent was removed by vacuum distillation at 145° C. and the product was filtered through diatomaceous earth.

EXAMPLE 3

Boron-Containing Phosphite of Bis(2-Hydroxyethyl)tallowamine

Part A

Approximately 370 g of bis-(2-hydroxyethyl)tallowamine (obtained as Ethomeen T/12 from Armak Chemical Co.) and 55 g of dimethyl hydrogen phosphite were charged to a 1 liter glass reactor equipped as with heater, agitator, provision for blanketing the vapor space with nitrogen and a Dean-Stark tube with condenser. The reactor contents were heated to 120° C. for 2 hours, 135° C. for 2 hours and 150° C. for 2½ hours, during which latter time evolution of methanol diminished and appeared to cease. The crude product was then vacuum stripped at about 150° C. to remove volatile materials.

Part B

Approximately 130 g of the intermediate of Part A, 100 g of toluene and 1 g of boric acid were charged to a 500 ml reactor equipped as generally described in Part A. The reactor contents were heated to about 155° C. over a period of about 4 hours until water evolution as a result of azeotropic distillation ceased. Approximately 8 g of water was collected. The solvent was removed by vacuum distillation at about 155° C. and the reactor contents were filtered through diatomaceous earth.

EXAMPLE 4

Boron-Containing Phosphite of Bis(2-Hydroxypropyl)oleylamine

Part A

Approximately 370 g of bis (2-hydroxypropyl)oleylamine (obtained as Propomeen O/12 from Armak Chemical Co.) and 55 g of dimethyl hydrogen phosphite were charged to a one liter reactor equipped as generally described in Example 3. The reactor contents were heated to 120° C. for 2 hours, 135° C. for 2 hours, and 150° C. for 2 hours, during which time evolution of methanol diminished and appeared to cease. The crude product was vacuum stripped at 150° C. for ¼ hour to remove volatile materials.

Part B

Approximately 190 g of the intermediate of Part A, 100 g of toluene and 30 g of boric acid were charged to a 1 liter reactor equipped as generally described in Part A. The reactor contents were heated to about 150° C. over a period of about 6 hours until water evolution as a result of azeotropic distillation ceased. The solvent was removed by vacuum distillation at about 150° C. and the reactor contents were filtered through diatomaceous earth.

EVALUATION OF PRODUCTS

The borated alkoxylated amine phosphites were blended into fully formulated synthetic and mineral oil based engine oil lubricants and evaluated using the Low Velocity Friction Apparatus Test. These formulations include polymeric succinimide dispersants, metallic phenates and sulfonates, zinc dithiophosphates (derived from low molecular weight alkanols) and polymeric viscosity index improving additives. As shown by the data below, these novel compositions are effective friction reducers.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$), Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12–13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4–8 microinches.

The results obtained are shown in Tables 1 and 2. The data in the tables are reported as percent reduction in coefficient of friction at two speeds. The friction-reducing ester additives were evaluated in a fully formulated mineral lubricating oil (Table 1) or 5W–30 synthetic lubricating oil (Table 2), each comprising an additive package including antioxidant, detergent and dispersant.

TABLE 1

| Friction Test Results Using Low Velocity Friction Apparatus | | |
|---|---|---|
| | | % Reduction in |
| | Additive | Coefficient of |
| | Conc. in | Friction at |
| | Base Fluid | 5 | 30 |
| | Weight % | Ft/Min | Ft/Min |
| Base Oil (fully formulated synthetic automotive engine oil containing detergent/dispersant/inhibitor performance package) SAE 5W30 | — | 0 | 0 |
| Example 1 Plus Base Oil | 2 | 29 | 25 |
| Example 2 Plus Base Oil | 2 | 27 | 26 |
| Example 3 Plus Base Oil | 2 | 27 | 20 |
| Example 4 Plus Base Oil | 2 | 29 | 18 |

TABLE 2

| Friction Test Results Using Low Velocity Friction Apparatus | | |
|---|---|---|
| | | % Reduction in |
| | Additive | Coefficient of |
| | Conc. in | Friction at |
| | Base Fluid | 5      30 |
| | Weight % | Ft/Min  Ft/Min |
| Base Oil (fully formulated mineral oil based automotive engine oil containing detergent/dispersant/inhibitor performance package) SAE 10W40 | — | 0      0 |
| Example 1 Plus Base Oil | 2 | 17     10 |
| Example 2 Plus Base Oil | 1 | 17     10 |
| Example 3 Plus Base Oil | 2 | 19     15 |
| Example 4 Plus Base Oil | 2 | 31     31 |

The copper strip corrosivity properties of the borated alkoxylated amine phosphites were evaluated in 200″ Solvent Paraffinic Neutral mineral oil.

TABLE 3

| Copper Strip Corrosivity Test Results | | |
|---|---|---|
| | ASTM | ASTM |
| Conc. of | D130-80 | D130-80 |
| Wt. % | 3 Hrs @ 250° F. | 6 Hrs @ 210° F. |
| Example 4 Plus Oil - Boron-containing phosphite of bis (2-hydroxypropyl) oleylamine  1.0 | 1A | 1A |

As is clearly demonstrated by the results, the high temperature stability of the products of the invention to copper is good.

We claim:

1. A product of reaction made by reacting (1) an alkoxylated amine of the formula

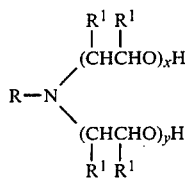

wherein R is a $C_6$ to $C_{30}$ hydrocarbyl group, $R^1$ is hydrogen or a $C_1$ to $C_6$ hydrocarbyl group, and x and y are integers of from 0 to 10, at least one of which is not 0 with (2) a phosphite of the formula

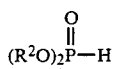

wherein $R^2$ is a $C_1$ to $C_6$ hydrocarbyl group, and (3) a boron compound selected from the group consisting of boric oxide, a metaborate, and a compound of the formula

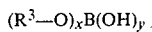

wherein $R^3$— is a $C_1$ to $C_6$ alkyl group and x and y are 0 to 3, their sum being 3.

2. The product of claim 1 wherein the $C_6$ to $C_{30}$ hydrocarbyl group is alkyl, aryl, alkenyl, alkaryl, aralkyl or cycloalkyl.

3. The product of claim 1 wherein $R^1$ is an alkyl group.

4. The product of claim 1 wherein $R^2$ is an alkyl group.

5. The product of claim 1 wherein the alkoxylated amine is 2-hydroxylethylhexylamine, 2-hydroxyethyloctylamine, 2-hydroxyethyldodecylamine, 2-hydroxyethyltetradecylamine, 2-hydroxyethylpentadecylamine, 2-hydroxyethyleicosylamine, 2-hydroxyethyltriacontylamine, 2-hydroxyethyloleylamine, 2-hydroxyethyltallowamine, 2-hydroxyethylsoyamine, bis(2-hydroxyethyl)hexylamine, bis(2-hydroxyethyl)octylamine, bis(2-hydroxyethyl)dodecylamine, bis(2-hydroxyethyl)tetradecylamine, bis(2-hydroxyethyl)pentadecylamine, bis(2-hydroxyethyl)eicosylamine, bis(2-hydroxyethyl)triacontylamine, bis(2-hydroxyethyl)oleylamine, bis(2-hydroxyethyl)tallowamine, bis(2-hydroxyethyl)soyamine, 2-hydroxypropylhexylamine, 2-hydroxypropyloctylamine, 2-hydroxypropyldodecylamine, 2-hydroxypropyltetradecylamine, 2-hydroxypropylpentadecylamine, 2-hydroxypropyleicosylamine, 2-hydroxypropyltriacontylamine, 2-hydroxypropyloleylamine, 2-hydroxypropyltallowamine, 2-hydroxypropylsoyamine, bis(2-hydroxypropyl)hexylamine, bis(2-hydroxypropyl)octylamine, bis(2-hydroxypropyl)dodecylamine, bis(2-hydroxypropyl)tetradecylamine, bis(2-hydroxypropyl)pentadecylamine, bis(2-hydroxypropyl)eicosylamine, (2-hydroxypropyl)triacontylamine, bis(2-hydroxypropyl)oleylamine, bis(2-hydroxypropyl)tallowamine, bis(2-hydroxypropyl)soyamine or mixtures thereof, and polyalkoxylated amines.

6. The product of claim 1 wherein the phosphite is dimethyl phosphite, diethyl phosphite, dipropyl phosphite, dibutyl phosphite, diamyl phosphite, dihexyl phosphite or mixtures thereof.

7. The product of claim 1 wherein the alkoxylated amine is bis(2-hydroxyethyl)oleylamine, the phosphite is dimethyl phosphite and the boron compound is boric acid.

8. The product of claim 1 wherein the alkoxylated amine is bis(2-hydroxyethyl)cocoamine, the phosphite is dimethyl phosphite and the boron compound is boric acid.

9. The product of claim 1 wherein the alkoxylated amine is bis(2-hydroxyethyl)soyamine, the phosphite is dimethyl phosphite and the boron compound is boric acid.

10. A lubricant composition comprising a major proportion of a lubricating oil or a grease and a friction reducing amount of a product of reaction made by reacting (1) an alkoxylated amine of the formula

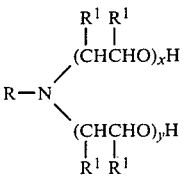

wherein R is a $C_6$ to $C_{30}$ hydrocarbyl group, $R^1$ is hydrogen or a $C_1$ to $C_6$ hydrocarbyl group, and x and y are integers of from 0 to 10, at least one of which is not 0 with (2) a phosphite of the formula $$(R^2O)_2\overset{\overset{O}{\|}}{P}-H$$

wherein $R^2$ is a $C_1$ to $C_6$ hydrocarbyl group, and (3) a boron compound selected from the group consisting of boric oxide, a metaborate, and a compound of the formula $$(R^3-O)_xB(OH)_y$$

wherein $R^3-$ is a $C_1$ to $C_6$ alkyl group and x and y are 0 to 3, their sum being 3.

11. The composition of claim 10 wherein the $C_6$ to $C_{30}$ hydrocarbyl group is alkyl, aryl, alkenyl, alkaryl, aralkyl or cycloalkyl.

12. The composition of claim 10 wherein $R^1$ is an alkyl group.

13. The composition of claim 10 wherein $R^2$ is an alkyl group.

14. The composition of claim 10 wherein the alkoxylated amine is 2-hydroxylethylhexylamine, 2-hydroxyethyloctylamine, 2-hydroxyethyldodecylamine, 2-hydroxyethyltetradecylamine, 2-hydroxyethylpentadecylamine, 2-hydroxyethyleicosylamine, 2-hydroxyethyltriacontylamine, 2-hydroxyethyloleylamine, 2-hydroxyethyltallowamine, 2-hydroxyethylsoyamine, bis(2-hydroxyethyl)hexylamine, bis(2-hydroxyethyl)octylamine, bis(2-hydroxyethyl)dodecylamine, bis(2-hydroxyethyl)tetradecylamine, bis(2-hydroxyethyl)pentadecylamine, bis(2-hydroxyethyl)eicosylamine, bis(2-hydroxyethyl)triacontylamine, bis(2-hydroxyethyl)oleylamine, bis(2-hydroxyethyl)tallowamine, bis(2-hydroxyethyl)soyamine, 2-hydroxypropylhexylamine, 2-hydroxypropyloctylamine, 2-hydroxypropyldodecylamine, 2-hydroxypropyltetradecylamine, 2-hydroxypropylpentadecylamine, 2-hydroxypropyleicosylamine, 2-hydroxypropyltriacontylamine, 2-hydroxypropyloleylamine, 2-hydroxypropyltallowamine, 2-hydroxypropylsoyamine, bis(2-hydroxypropyl)hexylamine, bis(2-hydroxypropyl)octylamine, bis(2-hydroxypropyl)dodecylamine, bis(2-hydroxypropyl)tetradecylamine, bis(2-hydroxypropyl)pentadecylamine, bis(2-hydroxypropyl)eicosylamine, bis(2-hydroxypropyl)triacontylamine, bis(2-hydroxypropyl)oleylamine, bis(2-hydroxypropyl)tallowamine, bis(2-hydroxypropyl)soyamine or mixtures thereof, and polyalkoxylated amines.

15. The composition of claim 10 wherein the phosphite is dimethyl phosphite, diethyl phosphite, dipropyl phosphite, dibutyl phosphite, diamyl phosphite, dihexyl phosphite or mixtures thereof.

16. The product of claim 10 wherein the alkoxylated amine is bis(2-hydroxyethyl)oleylamine, the phosphite is dimethyl phosphite and the boron compound is boric acid.

17. The product of claim 10 wherein the alkoxylated amine is bis(2-hydroxyethyl)cocoamine, the phosphite is dimethyl phosphite and the boron compound is boric acid.

18. The procuct of claim 10 wherein the alkoxylated amine is bis(2-hydroxyethyl)soyamine, the phosphite is dimethyl phosphite and the boron compound is boric acid.

19. The composition of claim 11 wherein the lubricant is (1) a mineral oil, (2) a synthetic oil or mixtures of synthetic oils, (3) a mixture of (1) and (2) or (4) a grease from (1), (2) or (3).

20. The composition of claim 19 wherein the lubricant is a mineral oil.

21. The composition of claim 19 wherein the lubricant is a synthetic oil or mixtures of synthetic oils.

22. The composition of claim 19 wherein the lubricant is the mixture of (3).

23. The composition of claim 19 wherein the lubricant is said grease.

24. A method of reducing fuel consumption in an internal combustion engine which comprises lubricating said engine with a lubricant composition comprising a major proportion of a lubricant and a fuel reducing amount of a product made by reacting (a) an alkoxylated amine of the formula $$R-N\begin{matrix}(\overset{R^1}{\underset{|}{C}}\overset{R^1}{\underset{|}{H}}CHO)_xH\\(\overset{R^1}{\underset{|}{C}}\overset{R^1}{\underset{|}{H}}CHO)_yH\end{matrix}$$

wherein R is a $C_6$ to $C_{30}$ hydrocarbyl group, $R^1$ is hydrogen or a $C_1$ to $C_6$ hydrocarbyl group, and x and y are integers of from 0 to 10, at least one of which is not 0 with (b) a phosphite of the formula $$(R^2O)_2\overset{\overset{O}{\|}}{P}-H$$

wherein R is a $C_1$ to $C_6$ hydrocarbyl group, and (c) a boron compound.

* * * * *

UNITED STATES PATENT AND TRADEMARK OFFICE
CERTIFICATE OF CORRECTION

PATENT NO.   :   4,529,528
DATED        :   July 16, 1985
INVENTOR(S)  :   Andrew G. Horodysky It is certified that error appears in the above-identified patent and that said Letters Patent is hereby corrected as shown below:

Column 1, line 8, change "proeducts" to --products--.

Column 3, line 11, change "tetradecylaminee" to --tetradecylamine--.

Column 6, line 3, change "alchols" to --alcohols--.

Column 10, line 29, insert --bis-- before "(2-...)".

Signed and Sealed this

Nineteenth Day of November 1985

[SEAL]

Attest:

Attesting Officer

DONALD J. QUIGG

Commissioner of Patents and Trademarks